United States Patent [19]
Sakairi et al.

[11] Patent Number: 5,633,496
[45] Date of Patent: May 27, 1997

[54] MASS SPECTROMETRY APPARATUS

[75] Inventors: Minoru Sakairi, Kawagoe; Tadao Mimura, Katsuta; Yoichi Ose, Mito; Atsumu Hirabayashi; Yasuaki Takada, both of Kokubunji, all of Japan

[73] Assignee: Hitachi, Ltd., Tokyo, Japan

[21] Appl. No.: 405,767

[22] Filed: Mar. 17, 1995

[30] Foreign Application Priority Data

Mar. 17, 1994 [JP] Japan .................... 6-046722

[51] Int. Cl.$^6$ .................... B01D 59/44; H01J 49/00
[52] U.S. Cl. .................... 250/288; 250/281
[58] Field of Search .................... 250/281, 288, 250/423 R

[56] References Cited

U.S. PATENT DOCUMENTS

| | | | |
|---|---|---|---|
| 4,144,451 | 3/1979 | Kambara | 250/281 |
| 4,888,482 | 12/1989 | Kato | 250/288 |
| 4,963,735 | 10/1990 | Okamoto et al. | 250/288 |
| 5,144,127 | 9/1992 | Williams et al. | 250/281 |
| 5,148,021 | 9/1992 | Okamoto et al. | 250/288 |
| 5,202,562 | 4/1993 | Koga et al. | 250/288 |
| 5,352,892 | 10/1994 | Mordehai et al. | 250/288 |
| 5,381,008 | 1/1995 | Tanner et al. | 250/288 |

*Primary Examiner*—Bruce C. Anderson
*Attorney, Agent, or Firm*—Antonelli, Terry, Stout & Kraus, LLP

[57] ABSTRACT

A mass spectrometry apparatus which includes an ion source which ionizes a sample under atmospheric pressure and outputs the ionized sample, a differential pumping region, provided with apertures, for receiving under vacuum ions in the ionized sample from the ion source and outputting the ions and an ion accelerating and focusing region, having a plurality of ion accelerating electrodes each having applied thereto a voltage, for accelerating and focusing under vacuum the ions from the differential pumping region. The ions from the accelerating and focusing region are introduced under vacuum to a mass spectrometer which detects and analyzes the ions.

21 Claims, 7 Drawing Sheets

F I G. 12
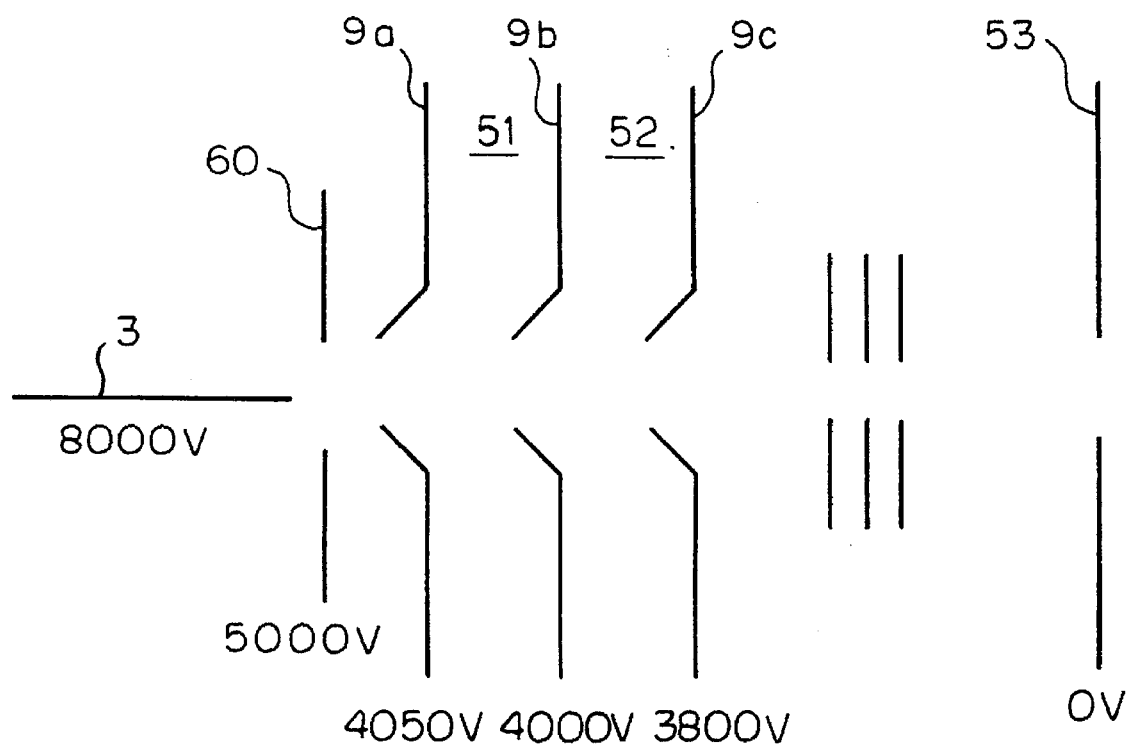

MASS SPECTROMETRY APPARATUS

BACKGROUND OF THE INVENTION

The present invention relates to a mass spectrometry apparatus. More particularly the present invention relates to a mass spectrometry apparatus suitable for ionizing a sample in a liquid and introducing the resultant ions into a mass spectrometer.

At present, apparatuses using liquid chromatography/mass spectrometry (which will hereinafter be abbreviated as LC/MS) and capillary electrophoresis/mass spectrometry (which will hereinafter be abbreviated as CE/MS) are considered to be new promising separation analyzers for Volatile or nonvolatile compounds. FIG. 9 is a construction diagram of a conventional LC/MS apparatus. A LC/MS apparatus is an analyzer using a mass spectrometer for a liquid chromatograph detector. The apparatus of FIG. 9 is a conventional example using a magnetic sector type mass spectrometer as a mass spectrometer, in which other types of mass spectrometers, such as a quadruple mass spectrometer, an ion trap mass spectrometer, an ion cyclotron resonance mass spectrometer and a time of flight mass spectrometer can also be used. In an analyzer using LC/MS, measurement is conducted generally as follows. A sample in a liquid separated by and sent out from a liquid chromatograph 1 is introduced sequentially into an ion source 22. The sample is ionized in this part to turn it into ions thereof. The ions thus generated are introduced into a magnetic sector type mass spectrometer consisting of an electric field 24 and a magnetic field 25 which are evacuated by vacuum pumps 23a, 23b, 23c, 23d, and are then mass separated. The mass separated ions are detected by a detector 26. A detected signal is amplified by an amplifier 27 and then sent to a data processor 28, in which it is subjected to mass spectrometry.

In the apparatus using LC/MS, the liquid chromatograph handles a sample in a liquid, while the mass spectrometer handles ions in a vacuum. Therefore, the important points of the development of an apparatus using LC/MS reside in techniques for ionizing a sample in a solution eluting from the liquid chromatograph 1. Some ionization methods have heretofore been proposed. A typical ionization method is an electrospray method disclosed in Japanese Patent Laid-Open Nos. 41747/1985 and 41748/1985. In the electrospray method, an apparatus shown in FIG. 10 is used. In this apparatus, a sample solution forced out by a suitable pump is introduced into a capillary 4 in an electrospray ion source 3. Usually, this capillary consists of a metal. When several kV of voltage is applied between this capillary 4 and a counter electrode 60, the sample solution becomes conical at a free end of the capillary, and an electrostatic atomization phenomenon in which a large number of fine droplets are formed at a free end of the cone.

A reference numeral 61 denotes a gas introduction port. When a gas, such as dry nitrogen is introduced into this port, the fine droplets are gasified with the gas blown out from a hole made in the counterelectrode 60, and ions occur in this process. These ions enter a differential pumping region 11 enclosed with a nozzle 7 and a skimmer 9 and evacuated by a roughing vacuum pump, and are introduced into a mass spectrometer under high vacuum through the skimmer 9, in which spectrometer the ions are subjected to mass spectrometry.

When the electrospray method is applied to a magnetic sector type mass spectrometer in which an accelerating voltage of not less than 1.5 kV is used, the following problems arise. The ions, fine droplets and neutral molecules generated by the electrospray method pass through the skimmer 9 in the differential pumping region 11 (pressure is not less than $10^{-3}$ Torr), and are blown into a vacuum (pressure is not more than $10^{-3}$ Torr) in which the mass spectrometer is provided. FIG. 11 shows the behavior of the ions 29 and neutral molecules 30 taken into the differential pumping region. When the ions 29 are accelerated by a high accelerating voltage immediately after they have passed through the skimmer, they have high kinetic energy and collide with residual neutral molecules 30. During this time, the kinetic energy of the ions is converted into internal energy. When the converted internal energy is large with the ions consisting of organic molecules, the decomposition of the organic molecules occur. Especially, when the ions generated consist of multiply charged ions (ions having a large number of electric charges), they give rise to problems. For example, even when the same ion accelerating voltage is used, the quantity of the kinetic energy obtained by ions of charge-state of +3 becomes thrice that of the kinetic energy obtained by ions of charge-state of +1. Accordingly, the ions of charge-stage of +3 collide with neutral molecules with large energy, and the ions become ready to be decomposed. In fact, when a quadruple mass spectrometer in which a low ion accelerating voltage (for example, 10 V) is used is employed, ions of charge-stage of +3 in which three protons are deposited on bradykinin molecules, ions of a kind of peptide by the electrospray method are clearly observed. However, when these ions of charge-state of +3 are accelerated at once at 4000 V and introduced into a magnetic sector type mass spectrometer in which an ion accelerating voltage (for example, 4000 V) is high, they are decomposed at a stroke to ions which occur when the bradykinin is decomposed. Therefore, when the ion accelerating voltage is high, it is difficult to determine the molecular weight of the bradykinin molecules.

A method of preventing such a phenomenon in which the ions are decomposed was made public in the American Academic Circle of Mass Spectrometry (The 39th ASMS Conference on Mass Spectrometry and Allied Topics, p. 244, 1991). FIG. 12 shows voltages applied to the electrospray ion source and differential pumping region used in this method. In addition to the first differential pumping region 51 (pressure is not less than $10^{-3}$ Torr) evacuated by a roughing pump, one more differential pumping region, i.e. a second differential pumping region 52 (pressure is the level of $10^{-4}$ Torr) evacuated by a turbomolecular pump is provided.

In the first differential pumping region 51, the number of neutral molecules is large, so that the ions collide with the neutral molecules repeatedly many times. The acceleration of ions in the first differential pumping region is substantially negligible. Therefore, the ions are substantially accelerated by a difference in voltage between a skimmer 9b and a slit 53. Accordingly, the ion accelerating voltage is equal to a difference in voltage between the skimmer 9b and slit 53.

In a method using two such differential pumping regions with an ion accelerating voltage of, for example, 4000 V employed, a voltage of 200 V is applied between skimmers 9b, 9c, and an ion accelerating voltage in the second differential pumping region 52 in which the vacuum is in the level of $10^4$ Torr is set lower. The remaining 3800 V is applied between the skimmer 9c and slit 53 so as to accelerate the ions in a region (pressure is not more than $10^{-6}$ Torr) ahead of the skimmer 9c in which the collision of ions with neutral molecules less frequently occurs, whereby the decomposition of the ions ascribed to the collision of ions with neutral molecules is minimized.

In a conventional method using two differential pumping regions, it is necessary to provide a differential pumping region. This causes the apparatus to be enlarged and complicated. There is also a problem that the ion transmission efficiency decreases greatly in the differential pumping region with the sensitivity of the apparatus thereby lowered.

SUMMARY OF THE INVENTION

An object of the present invention is to provide a mass spectrometry apparatus which is capable of attaining ion acceleration which permits ions to be introduced into a mass spectrometer efficiently, without providing a differential pumping region, and which is designed so that the decomposition of ions ascribed to the collision of ions with neutral molecules is minimized.

To achieve this object, the present invention provides a mass spectrometry apparatus having an ion source which ionizes a sample under atmospheric pressure or a pressure equivalent thereto and outputs the ionized sample to a mass spectrometer for detecting and analyzing under vacuum the ions generated in the ion source, a differential pumping region provided with apertures for receiving ions under vacuum from the ion source and outputting the ions and an ion accelerating and focusing region, having a plurality of ion accelerating electrodes each having applied thereto a voltage, for acceleration and focusing the ions from the differential pumping region into the mass spectrometer under vacuum.

Different voltages are applied independently to all of accelerating electrodes. The ion accelerating electrodes may include a first ion accelerating electrode (which will hereinafter be referred to as an ion extracting electrode) which is provided in the vicinity of an aperture in a differential pumping region through which ions pass when they are introduced into a space provided with a mass spectrometer, and which receives a fixed voltage. The ion accelerating electrodes may also include at least one ion accelerating electrode to which a voltage is applied in a varying manner so as to regulate an ion focusing distance by accelerating ions.

One of the ion accelerating electrodes may be a housing constituting an electron impact ionization source. An electrostatic lens or an ion deflecting electrode may be provided between the ion accelerating and focusing region and mass spectrometer. At least one of the ion accelerating electrodes may be a cylindrical electrode. The cylindrical electrode may consist of a cylindrical electrode provided with a vent hole, or a cylindrical electrode at least a part of which is provided with meshes. The ion accelerating electrodes may be heated by a heater provided on at least one of the electrodes.

The end portion of the ion extracting electrode which is on the side of the differential pumping region may be spherically formed. This end portion may be provided in a portion less than a predetermined distance away from the aperture in the differential pumping region, and the other end portion thereof which is on the side of the mass spectrometer in a position more than that predetermined distance away from the predetermined distance. This predetermined distance is set to a level determined by an expression 0.67×(inner diameter of the aperture)×(√(pressure in the differential pumping region)/(pressure in the region in which a plurality of ion accelerating electrodes are provided))), and the intensity of an electric field between the aperture in the differential pumping region and ion extracting electrode is preferably set to a level in the range from 0–2000 V/cm. The ion accelerating electrodes may be formed so as to include an einzel lens, and the material of these electrodes may be a metal.

According to the present invention, it is possible to accelerate an ionized sample at a low voltage immediately after it has been introduced from an aperture of a differential pumping region, in which the pressure is not lower than $10^{-3}$ Torr, transfer the resultant ions to a position distant from the aperture in the differential pumping region and greatly accelerate the ions in a position of a suitable degree of vacuum where the pressure is not higher than $10^{-6}$ Torr, by regulating the voltage applied to the ion accelerating electrodes, without providing another differential pumping region.

Immediately after the ionized sample is extracted from the aperture of the differential pumping region in which the pressure is not lower than $10^{-3}$ Torr into a high vacuum region, the quantity of residual neutral molecules is large. Therefore, the extraction of the ions is carried out at a low voltage between the aperture and ion extracting electrode. The extracted ions are then taken out without a loss and without being accelerated to a high vacuum of not higher than $10^{-6}$ Torr by the cylindrical electrode, and they are thereafter accelerated at a high voltage. The accelerated sample can be introduced into the mass spectrometer without causing it to collide with neutral molecules many times, and subjected to mass spectrometry.

BRIEF DESCRIPTION OF THE DRAWINGS

The present invention will be more apparent from the following detailed description, when taken in conjunction with the accompanying drawings, in which:

FIG. 12 is a drawing illustrating an electrospray ion source and voltages applied to the electrodes arranged in a differential pumping region in a conventional apparatus.

DETAILED DESCRIPTION OF THE PREFERRED EMBODIMENTS

The embodiments of the present invention will now be described in detail with reference to the drawings.

Figure 1:
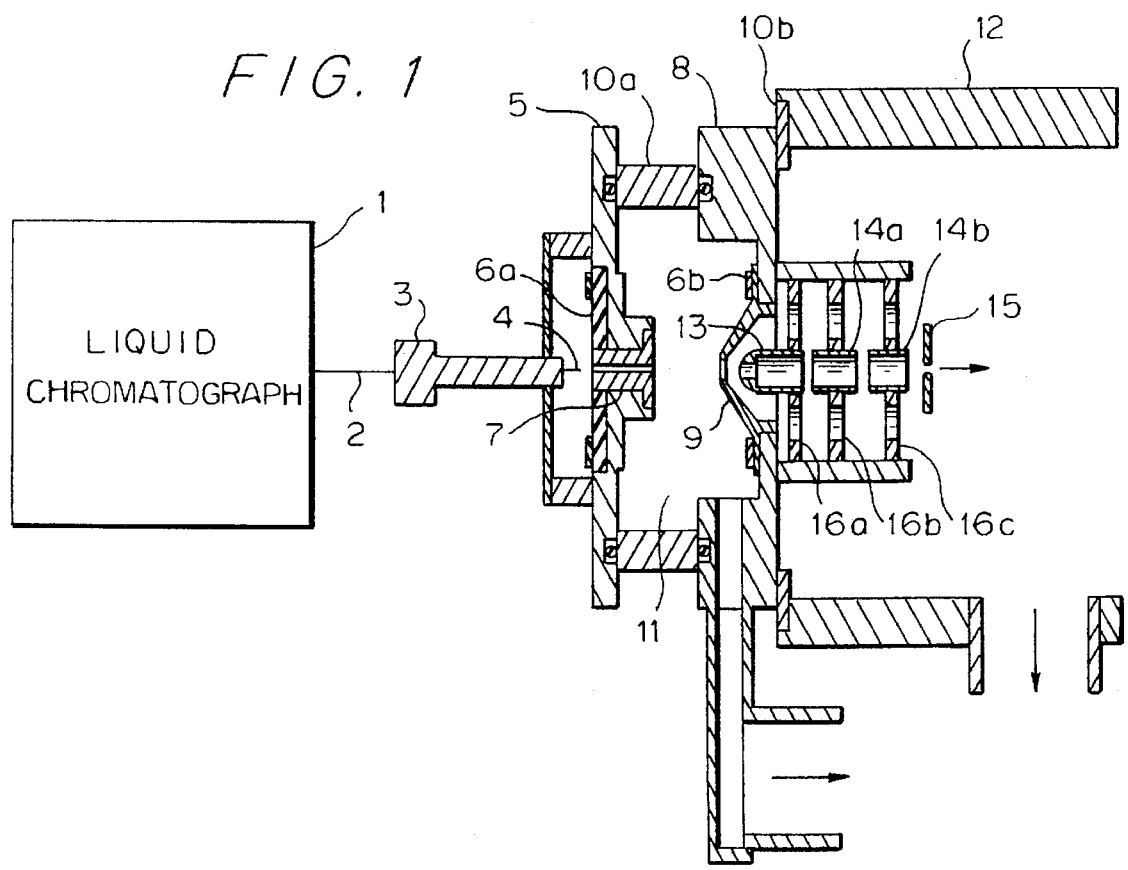
FIG. 1 is a sectional view illustrating the construction of an embodiment of the apparatus according to the present invention.

FIG. 1 shows an embodiment of the LC/MS apparatus according to the present invention. This embodiment shows an example to which an ion source 3 using an electrospray method is applied. In the apparatus of this construction, an ion source using some other atmospheric pressure ionization method, such as an atmospheric pressure chemical ionization method utilizing corona discharge can also be employed. A capillary electrophoresis apparatus can also be used instead of a liquid chromatograph 1. The apparatus of this construction can also be applied to flow injection mass spectrometry carried out by introducing a sample solution continuously into an ion source 3 by using a suitable pump.

A sample separated by the liquid chromatograph 1 passes through a flow passage 2 and enters the ion source 3 using the electrospray method. The fine droplets generated at a free end of a capillary 4 in the ion source 3 are held by a first-flange 5 and pass through a nozzle 7 heated with a heater 6a. In general, the nozzle 7 is heated to not lower than 70° C. and the inner diameter and length thereof are set to 0.25 mm and as large as around 20 mm respectively. The fine droplets are substantially gasified while they pass through the heated nozzle 7, and the ions of the sample contained in the fine droplets are generated. The generated ions are held by a second flange 8 and pass through a skimmer 9 heated with a heater 6b.

The first and second flanges 5, 8 are electrically insulated from each other via an insulating member 10a, so that voltages can be applied thereto independently. The second flange 8 is also electrically insulated from a housing 12, in which a mass spectrometer body is provided, via an insulating member 10b. A differential pumping region 11 provided between the nozzle 7 and skimmer 9 is evacuated by a roughing vacuum pump through a vacuum pipe. Although this embodiment has only one differential pumping region 11, a plurality of differential pumping regions may be provided.

The ions passed through the skimmer 9 are extracted from the differential pumping region 11 by a voltage applied between the skimmer 9 and an ion extracting electrode 13 (first ion accelerating electrode) retained by a support 16a, and then accelerated. The ions are thereafter accelerated again by a voltage applied between the ion extracting electrode 13 and a cylindrical electrode 14a retained by a support 16b. The ions are accelerated for the third time by a voltage applied between the cylindrical electrode 14a and a cylindrical electrode 14b retained by a support 16c. When a voltage is applied between the cylindrical electrode 14b and a slit 15 having ion collimating function and is at ground potential, the ions are further accelerated.

For example, in order to operate a magnetic sector type mass spectrometer with a 4000 V ion accelerating voltage, voltages to be applied to the electrodes for the purpose of observing positive ions are discussed. Since the degree of vacuum in the differential pumping region 11 is usually in the range of 0.1–10 Torr, a large quantity of molecules reside therein. Even when the ions are accelerated in this region, they collide with the residual molecules and are not substantially accelerated. The region in which the ions are accelerated is a region of a degree of vacuum of not less than $10^{-4}$ Torr, i.e. a region on the side of the mass spectrometer and on the downstream side of the skimmer 9. In order to increase the ion transmission efficiency, a potential difference between the nozzle 7 and skimmer 9 is set to zero to around 200 V, and a 4000 V ion accelerating voltage is applied between the skimmer 9 and slit 15.

Figure 10:
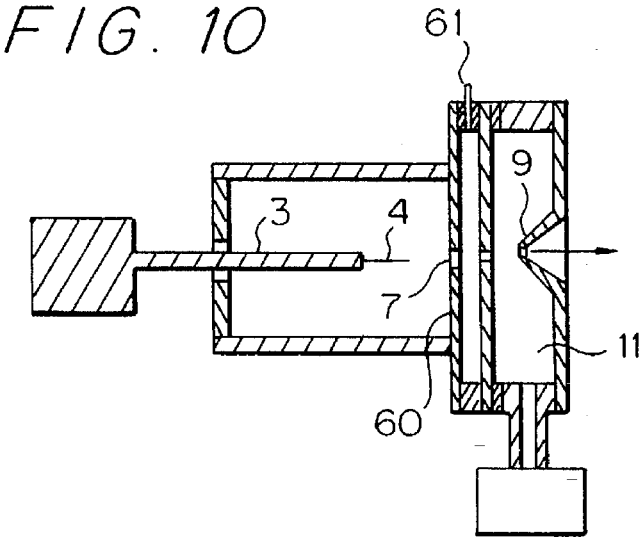
FIG. 10 is a sectional view of conventional examples of an electrospray ion source and a differential pumping region.
Figure 11:
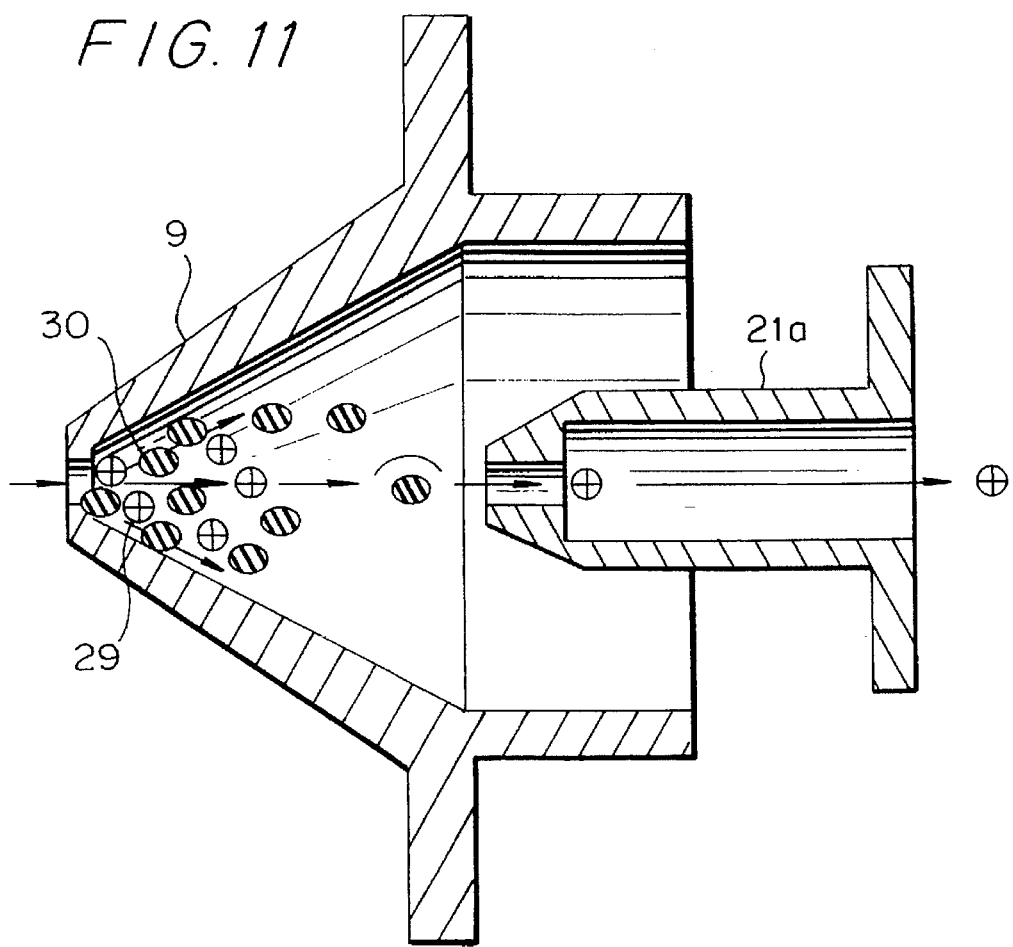
FIG. 11 is a drawing illustrating the behavior of the ions and neutral molecules taken into the inner side of a skimmer.

When the ion accelerating voltage is as high as 4000 V, the ions and neutral molecules collide with one another immediately after the ions pass through the skimmer 9, and the ions are decomposed to cause problems to arise (refer to FIG. 10). Immediately after the skimmer 9, a region of a high molecular concentration is formed. This region is called a supersonic region, and known as a region from the diameter of the aperture of the skimmer to {0.67×(diameter of the aperture of the skimmer)×(√(Pressure in the differential pumping region)/(pressure in the portion in which the cylindrical electrode 14 is provided)))}. When a voltage applied to the skimmer 9 and that applied to the ion extracting electrode 13 are set to 4000 V and 0 V respectively, ions collide with molecules and are decomposed in the supersonic region of a high molecular concentration, so that it is impossible to set the voltage applied to the ion extracting electrode 13 to 0 V. Therefore, the efficiency of extracting ions from the differential pumping region 11 can be increased by setting low a potential difference between the skimmer 9 and ion extracting electrode 13 and setting a free end of the ion extracting electrode close to the skimmer 9.

Figure 2:
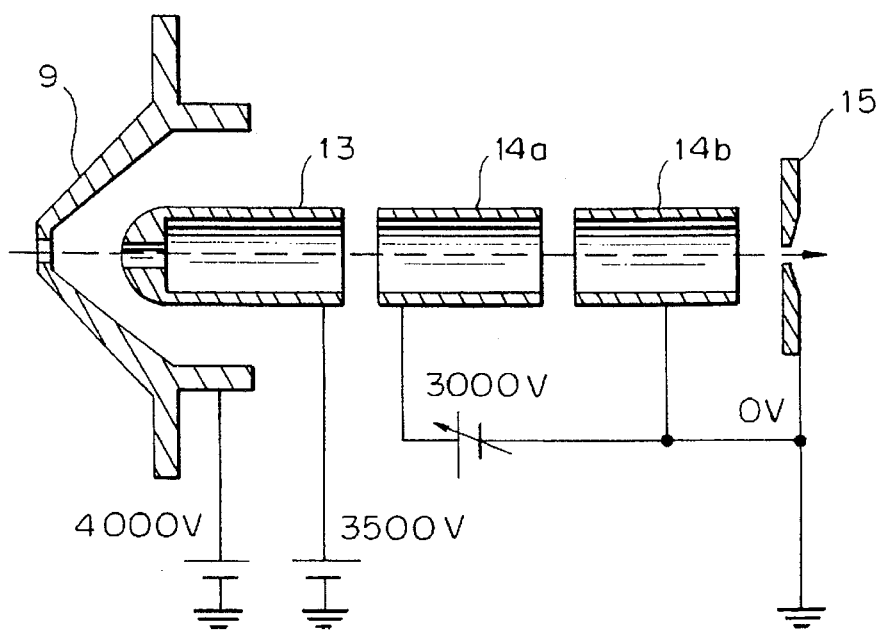
FIG. 2 is a drawing illustrating an example of voltages to be applied to various electrodes in the apparatus of FIG. 1.

FIG. 2 shows examples of voltages applied to various portions of the apparatus according to the present invention. In order to observe positive ions at a 4000 V ion accelerating voltage, 4000 V, 3500 V, 3000 V and 0 V are applied to the skimmer 9, ion extracting electrode 13, cylindrical electrode 14a and cylindrical electrode 14b respectively to obtain a 4000 V ion accelerating voltage. The potential difference between the skimmer 9 and ion extracting electrode 13 is 500 V, the potential difference between the ion extracting electrode 13 and cylindrical electrode 14a 500 V, and the potential difference between the cylindrical electrodes 14a, 14b 3000 V, so that the sum of all of these potential differences becomes equal to the ion accelerating voltage of 4000 V. The generation of electric discharge at the free end of the ion extracting electrode 13 can be prevented by spherically forming the free end portion of the same electrode 13 which is on the side of the skimmer 9.

In the example of voltage application shown in FIG. 2, a low voltage (500 V) is applied between the skimmer 9 and ion extracting electrode 13 in the region immediately after the skimmer 9 to extract ions from the differential pumping region 11 shown in FIG. 1. Therefore, a loss due to the decomposition of ions in the region immediately after the skimmer 9 can be prevented. The end of the cylindrical electrode 14a which is on the side of the cylindrical electrode 14b is positioned outside a supersonic region. The cylindrical electrode 14a efficiently transports ions to outside the supersonic region. The ions can be accelerated efficiently without a loss outside the supersonic region by applying 3000 V between the cylindrical electrodes 14a, 14b. When the voltage application is carried out so that the electric potential substantially decreases from the skimmer 9 toward the slit 15 as in the case of the example of voltage application shown in FIG. 2, the ions can be introduced into the mass spectrometer efficiently. For example, in order to observe negative ions, voltages of a polarity, which is opposite to that of the applied voltages in the case of the example of voltage application shown in FIG. 2, are applied to various electrodes, whereby the ions can be introduced into the mass spectrometer efficiently.

Figure 3A:
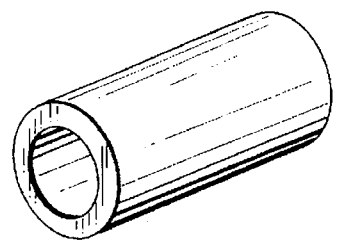
FIG. 3A is a drawing illustrating a regular cylindrical electrode.
Figure 3B:
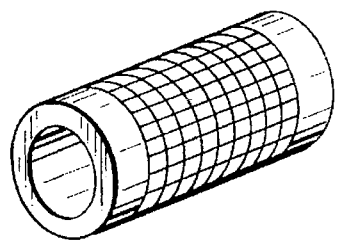
FIG. 3B is a drawing showing a cylindrical electrode provided with mesh.
Figure 3C:
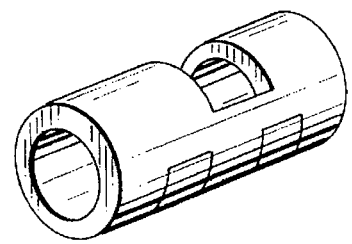
FIG. 3C is a drawing illustrating a cylindrical electrode provided with vent holes.

FIG. 3A shows a regular cylindrical electrode. The accelerating and focusing of ions are done between the cylindrical electrodes 14a, 14b in use, and the ions can be transmitted to a distant position by increasing the length of the cylindrical bodies thereof. When the voltage applied to the cylindrical electrode 14a is changed with the voltage applied to the ion extracting electrode 13 fixed, the focal distance of the ions can be changed. When an elongated cylindrical electrode is used as the cylindrical electrode 14a, it is formed so that at least a part of its cylindrical body consists of mesh as shown in FIG. 3B, or so that it has vent holes in its cylindrical body as shown in FIG. 3C, whereby a decrease in the degree of vacuum in the cylindrical electrode can be prevented.

Figure 4:
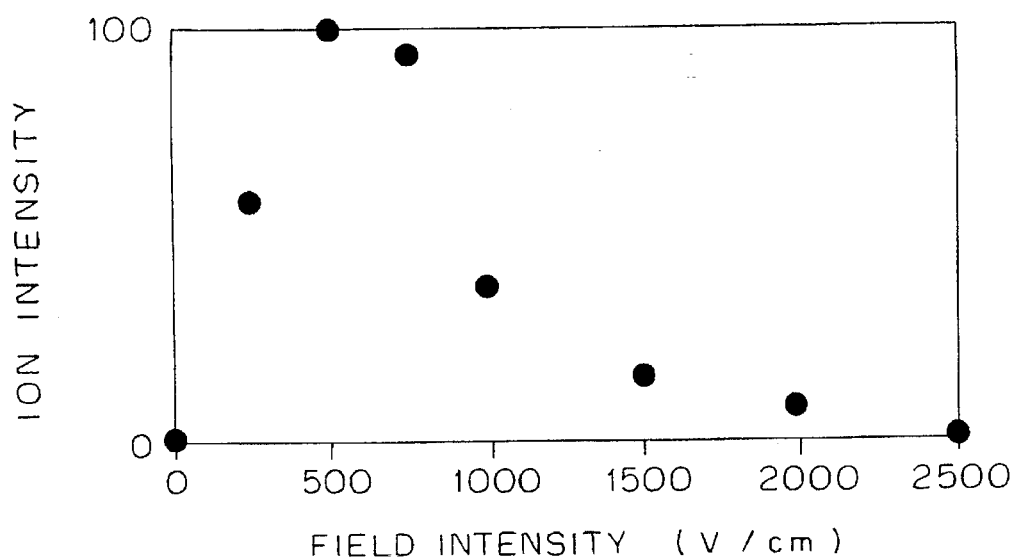
FIG. 4 is a graph illustrating the results of measurement conducted by the apparatus according to the present invention.

The ions of charge-state of +3 in each of which three protons are bonded to bradykinin molecules, a kind of peptide are measured by using the same apparatus as shown in FIG. 1. FIG. 4 shows the relation between the intensity of electric field between the aperture of the skimmer 9 and ion extracting electrode 13 and the intensity of ions of charge-state of +3 of bradykinin. The ions of charge-state of +3 begin to be observed when the electric field is not more than 2000 V/cm, and the intensity of these ions becomes maximum when the intensity of electric field is in the vicinity of 500 V/cm, the intensity of the ions decreasing conversely when the intensity of electric field is not more than around 500 V/cm. When the intensity of electric field is low, the ion extracting efficiency and the intensity of ions decrease.

Figure 5A:
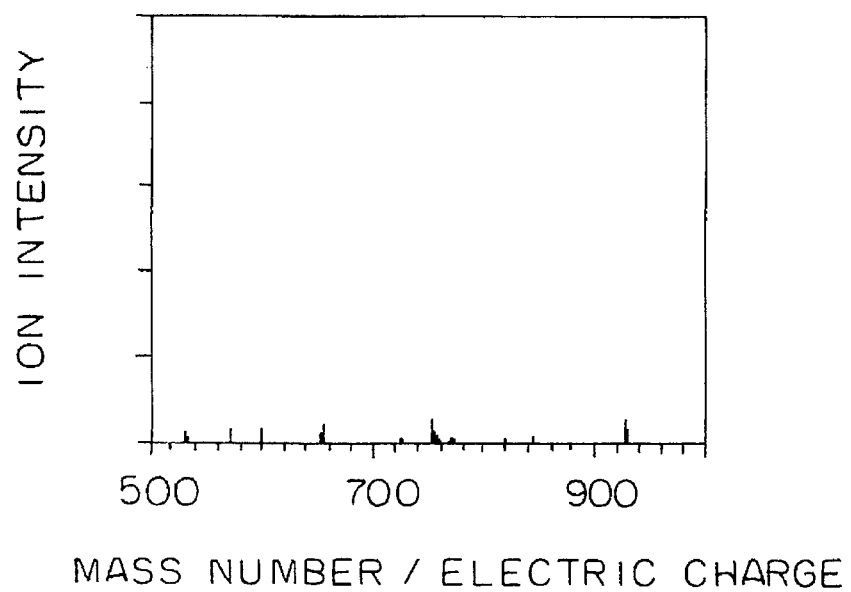
FIGS. 5A and 5B are graphs illustrating the results of other kinds of measurement conducted by apparatus according to the present invention.
Figure 5B:
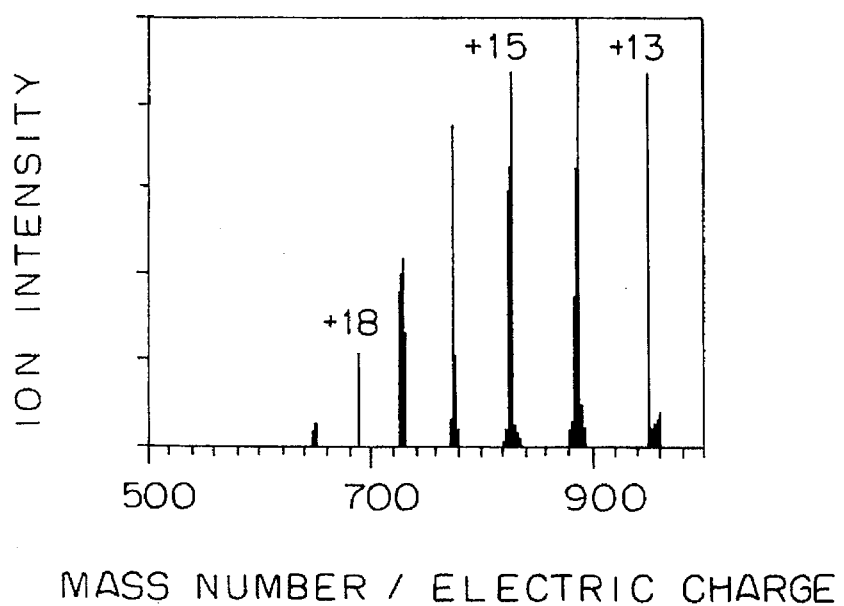

The above-described apparatus is very effective, especially, when the ions liable to be decomposed, such as ions of protein are measured. FIG. 5 shows the results of an example of measurement of myoglobin, a kind of protein by using the above-described apparatus. FIG. 5A shows a mass spectrum in a case where measurement is conducted with the ion accelerating voltages allotted in the above-mentioned manner. FIG. 5B shows a mass spectrum in a case where ions are accelerated at once by applying 4000 V and 0 V to the skimmer 9 and ion extracting electrode 13, respectively. The spectrum of FIG. 5B shows that multiple charged ions, such as ions of charge-state of +18, ions of charge-state of +15 and ions of charge state of +13 of myoglobin are observed clearly. In the spectrum of FIG. 5A, ions are not substantially observed since the decomposition of ions occurs. Accordingly, it is understood that using the above described apparatus with a divided ion accelerating voltage application system is effective.

Figure 6:
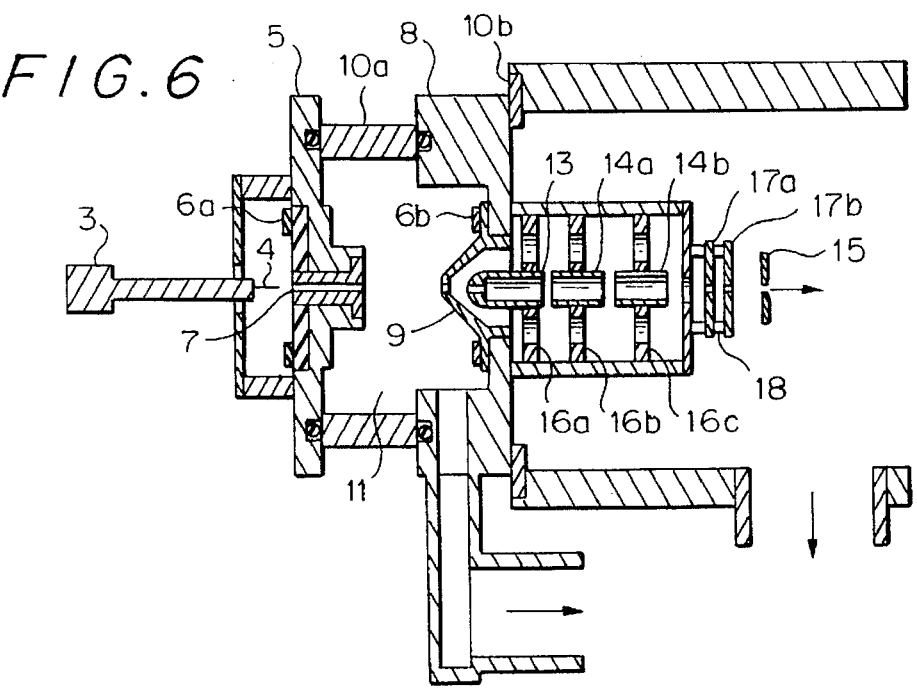
FIG. 6 is a sectional view of a second embodiment of the apparatus according to the present invention.

FIG. 6 is a sectional view of another embodiment of the present invention. In this embodiment, ion beam deflecting electrodes 17a, 17b are provided behind the cylindrical electrodes 14a, 14b. These deflecting electrodes 17a, 17b are preferably provided between these cylindrical electrodes and a slit 15. A deviation of the direction in which the ions advance in a case where the ion extracting electrode 13 and cylindrical electrodes 14a, 14b are set is eliminated by the deflecting electrodes 17a, 17b. The ions are deflected to two directions which are perpendicular to the direction of advancement of the ions, so as to minimize an ion loss, whereby the ions can be introduced efficiently into the mass spectrometer through the slit 15.

Figure 7:
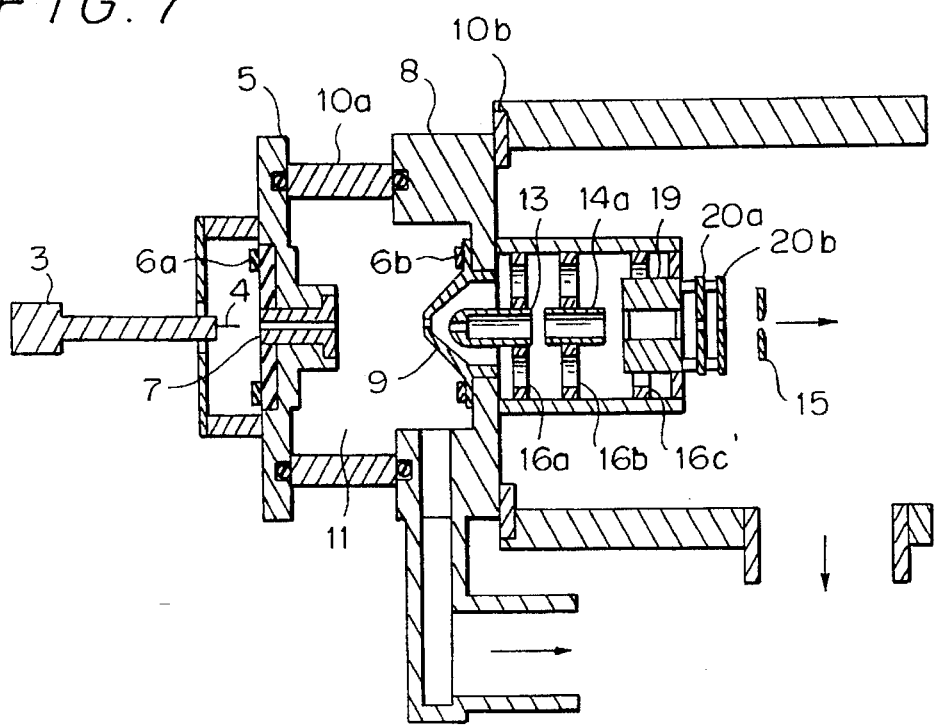
FIG. 7 is a sectional view of a third embodiment of the apparatus according to the present invention.

FIG. 7 is a sectional view of still another embodiment of the present invention. In this embodiment, a housing 19 constituting an electron impact ionization source is used as an electrode instead of the cylindrical electrode 14b shown in FIG. 6, and focusing electrodes 20a, 20b, which are to be combined with the electron impact ionization source, instead of the deflecting electrodes 17a, 17b. These focusing electrodes 20a, 20b are preferably provided between the housing 19 and a slit 15. Owing to the focusing electrodes 20a, 20b, ions can be introduced into a mass spectrometer efficiently through the slit 15 and without an ion loss. A measurement mode using an electron impact ionization source is normally provided in a regular magnetic sector type mass spectrometer, and, when this is utilized effectively, ions can be introduced into a mass spectrometer efficiently through the slit 15 and without an ion loss.

Figure 8:
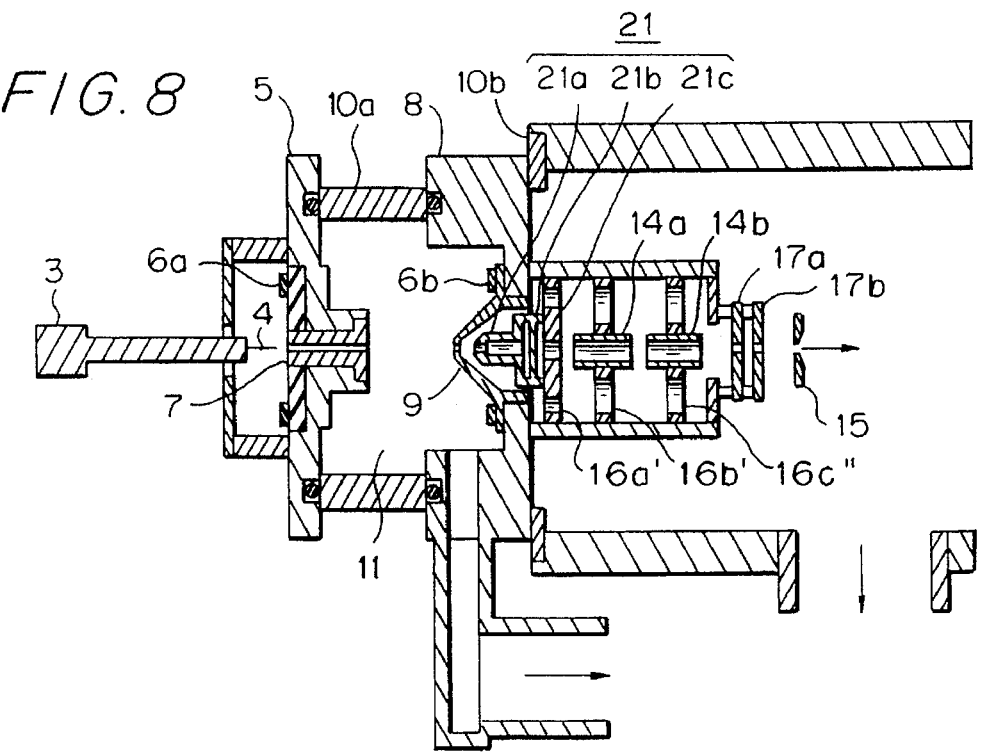
FIG. 8 is a sectional view of a fourth embodiment of the apparatus according to the present invention.
Figure 9:
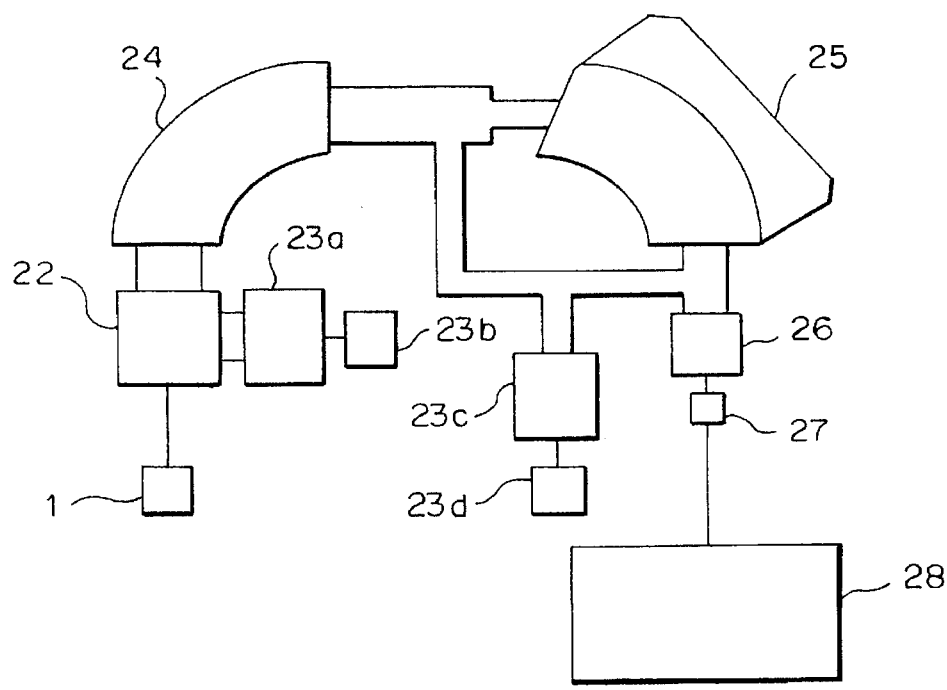
FIG. 9 is a diagram of a conventional example of a LC/MS using a magnetic sector type mass spectrometer.

FIG. 8 is a sectional view of a further embodiment of the present invention. In this embodiment, an einzel lens 21 is used instead of the ion extracting electrode L3 shown in FIG. 6, to focus the ions. In general, an einzel lens includes three series-arranged electrodes, and a voltage different from identical voltages applied to the electrodes on both sides is applied to the central electrode. The ions are extracted from a differential pumping region 11 by the einzel lens 21a through a skimmer 9, and decelerated between the einzel lenses 21a, 21b. The ions are then accelerated between the einzel lenses 21b, 21c. During this time, the focal distance can be varied freely by fixing the voltage applied to the einzel lenses 21a, 21c with the voltage to be applied to the einzel lens 21b set variable. After the ions have passed through these einzel lenses, they are accelerated by applying a higher voltage to cylindric lenses 14a, 14b. Thus, the ions can be introduced efficiently into a mass spectrometer as the decomposition of the ions is prevented.

As is clear from the above-described embodiments, the present invention enables the ions to be introduced from the skimmer 9 into the mass spectrometer efficiently by a simple structure without causing the ions to be decomposed even when the ion accelerating voltage is high. In the above-described embodiments, the ion accelerating voltage is divided into three, and it may be divided into a larger number of parts.

It is desirable that the ion extracting electrode 13 and cylindrical electrodes 14a, 14b in the above described embodiments be provided with a heater. For example, heaters may be incorporated into the supports 16a, 16b, 16c so as to heat the electrodes indirectly.

In these embodiments, apparatuses employing LC/MS are described, and, even in an apparatus employing CE/MS in which CE is used instead of LC, ions can be introduced into a mass spectrometer efficiently as the decomposition of the ions is prevented. Even when a flow injection method, in which a sample solution introduced continuously into a mass spectrometer is analyzed with a separating means not provided on a stage prior to MS, is employed, the ions can be introduced into the mass spectrometer efficiently as the decomposition of the ions is prevented.

In the above-described embodiments, a magnetic sector type mass spectrometer is used as a mass spectrometer. Thus, the same effect is obtained even when some other mass spectrometer, such as a quadruple mass spectrometer, a time of flight mass spectrometer, an ion trap mass spectrometer or an ion cyclotron resonance mass spectrometer is used.

According to the present invention, accelerating voltage can be applied in a divided manner to the ions. Therefore, even when the ion accelerating voltage is high, the ions generated under an atmospheric pressure can be efficiently introduced into a mass spectrometer without causing the ions to be decomposed and without using a complicated differential pumping system.

While the present invention has been described in detail and pictorially in the accompanying drawings it is not limited to such details since many changes and modifications recognizable to those of ordinary skill in the art may be made to the invention without departing from the spirit and the scope thereof.

What is claimed is:

1. A mass spectrometry apparatus comprising:

an ion source which ionizes a sample under atmospheric pressure and outputs the ionized sample;

a differential pumping region, provided with apertures, for receiving under vacuum ions in the ionized sample from said ion source and outputting the ions;

an ion accelerating and focusing region, having a plurality of ion accelerating electrodes each having applied thereto a voltage, for accelerating and focusing under vacuum the ions from said differential pumping region; and a mass spectrometer for detecting and analyzing under vacuum the ions from said accelerating and focusing region;

wherein at least one of said plurality of ion accelerating electrodes is a cylindrical electrode;

wherein said cylindrical electrode includes a part having a mesh structure.

2. A mass spectrometry apparatus comprising:

an ion source which ionizes a sample under atmospheric pressure and outputs the ionized sample;

a differential pumping region, provided with apertures, for receiving under vacuum ions in the ionized sample from said ion source and outputting the ions;

an ion accelerating and focusing region, having a plurality of ion accelerating electrodes each having applied thereto a voltage, for accelerating and focusing under vacuum the ions from said differential pumping region; and a mass spectrometer for detecting and analyzing under vacuum the ions from said accelerating and focusing region;

wherein a pressure in said differential pumping region is not lower than $10^{-3}$ Torr, and a pressure in said ion accelerating and focusing region is not higher than $10^{-3}$ Torr;

wherein at least one of said plurality of ion accelerating electrodes is a cylindrical electrode;

wherein said cylindrical electrode includes a part having a mesh structure.

3. A mass spectrometry apparatus comprising:

an ion source which ionizes a sample under atmospheric pressure and outputs the ionized sample;

a differential pumping region, provided with apertures, for receiving under vacuum ions in the ionized sample from said ion source and outputting the ions;

an ion accelerating and focusing region, having a plurality of ion accelerating electrodes each having applied thereto a voltage, for accelerating and focusing under vacuum the ions from said differential pumping region; and a mass spectrometer for detecting and analyzing under vacuum the ions from said accelerating and focusing region;

wherein different voltages are applied independently to said ion accelerating electrodes;

wherein at least one of said plurality of ion accelerating electrodes is a cylindrical electrode;

wherein said cylindrical electrode includes a part having a mesh structure.

4. A mass spectrometry apparatus comprising:

an ion source which ionizes a sample under atmospheric pressure and outputs the ionized sample;

a differential pumping region, provided with apertures, for receiving under vacuum ions in the ionized sample from said ion source and outputting the ions;

an ion accelerating and focusing region, having a plurality of ion accelerating electrodes each having applied thereto a voltage, for accelerating and focusing under vacuum the ions from said differential pumping region; and a mass spectrometer for detecting and analyzing under vacuum the ions from said accelerating and focusing region;

wherein at least one of said plurality of ion accelerating electrodes is provided with a heater.

5. A mass spectrometry apparatus comprising:

an ion source which ionizes a sample under atmospheric pressure and outputs the ionized sample;

a differential pumping region, provided with apertures, for receiving under vacuum ions in the ionized sample from said ion source and outputting the ions;

an ion accelerating and focusing region, having a plurality of ion accelerating electrodes each having applied thereto a voltage, for accelerating and focusing under vacuum the ions from said differential pumping region; and a mass spectrometer for detecting and analyzing under vacuum the ions from said accelerating and focusing region;

wherein a pressure in said differential pumping region is not lower than $10^{-3}$ Torr, and a pressure in said ion accelerating and focusing region is not higher than $10^{-3}$ Torr;

wherein at least one of said plurality of ion accelerating electrodes is provided with a heater.

6. A mass spectrometry apparatus comprising:

an ion source which ionizes a sample under atmospheric pressure and outputs the ionized sample;

a differential pumping region, provided with apertures, for receiving under vacuum ions in the ionized sample from said ion source and outputting the ions;

an ion accelerating and focusing region, having a plurality of ion accelerating electrodes each having applied thereto a voltage, for accelerating and focusing under vacuum the ions from said differential pumping region; and a mass spectrometer for detecting and analyzing under vacuum the ions from said accelerating and focusing region;

wherein different voltages are applied independently to said ion accelerating electrodes;

wherein at least one of said plurality of ion accelerating electrodes is provided with a heater.

7. A mass spectrometry apparatus comprising:

an ion source which ionizes a sample under atmospheric pressure and outputs the ionized sample;

a differential pumping region, provided with a skimmer, for receiving under vacuum ions in the ionized sample output form said ion source and outputting the received ions through said skimmer;

an ion accelerating region, having a plurality of ion accelerating electrodes, for accelerating under vacuum the ions output from said differential pumping region; and a mass spectrometer for detecting and analyzing under vacuum the ions from said accelerating region, wherein said plurality of ion accelerating electrodes are serially arranged between said skimmer and said mass spectrometer, each accelerating electrode having applied thereto a constant voltage which is different from other constant voltages applied to the other accelerating electrodes such that kinetic energy of the accelerated ions are continually increased toward the side of said mass spectrometer.

8. A mass spectrometry apparatus according to claim 7, wherein the voltage difference between said skimmer and the accelerating electrodes provided adjacent to said skimmer is smaller than the voltage difference between the other two ion accelerating electrodes provided adjacent to said mass spectrometer.

9. A mass spectrometry apparatus according to claim 7, wherein one of said plurality of ion accelerating electrodes includes a housing having an electron impact ionization source.

10. A mass spectrometry apparatus according to claim 7, wherein an ion deflector is provided between said ion accelerating region and said mass spectrometer.

11. A mass spectrometry apparatus according to claim 7, wherein at least one of said plurality of ion accelerating electrodes is a cylindrical electrode.

12. A mass spectrometry apparatus according to claim 11, wherein said cylindrical electrode is a bore carrying cylindrical electrode.

13. A mass spectrometry apparatus according to claim 11, wherein said cylindrical electrode includes a part having a mesh structure.

14. A mass spectrometry apparatus according to claim 7, wherein said plurality of ion accelerating electrodes includes a first ion accelerating electrode provided near said skimmer, and an end portion of said first ion accelerating electrode, which is on the side of said differential pumping region, has a hemispherical structure.

15. A mass spectrometry apparatus according to claim 14, wherein said end portion of said first ion accelerating electrode is provided at a position less than a predetermined distance away from said skimmer, and the other end portion of said first ion accelerating electrode which is on the side of said mass spectrometer is provided at a position more than said predetermined distance away from said skimmer.

16. A mass spectrometry apparatus according to claim 15, wherein said predetermined distance is a distance determined by an expression 0.67×the inner diameter of the aperture of said skimmer×the square root of (a pressure in said differential pumping region/a pressure in said ion accelerating region).

17. A mass spectrometry apparatus according to claim 7, wherein said plurality of ion accelerating electrodes include a first ion accelerating electrode provided near said skimmer, and a fixed voltage is applied to said first ion accelerating electrode to form an electric field in a range of 0–2000 V/cm, between said skimmer and said first ion accelerating electrode.

18. A mass spectrometry apparatus according to claim 7, wherein the pressure in said differential pumping region is not lower than $10^{-3}$ Torr, and the pressure in said ion accelerating region is not higher than $10^{-3}$ Torr.

19. A mass spectrometry apparatus according to claim 7, wherein at least one of said plurality of ion accelerating electrodes is provided with a heater.

20. A mass spectrometry apparatus for analyzing multiple charged ions obtained from organic matter comprising:

an ion source which ionizes a sample under atmospheric pressure and outputs the ionized sample;

a differential pumping region, provided with a skimmer, for receiving under vacuum ions in the ionized sample output from said ion source and outputting the received ions through said skimmer;

an ion accelerating region, having a plurality of ion accelerating electrodes, for accelerating under vacuum the ions output form said differential pumping region; and a mass spectrometer for detecting and analyzing under vacuum the ions from said ion accelerating region, wherein said plurality of ion accelerating electrodes are serially arranged between said skimmer and said mass spectrometer each accelerating electrode having applied thereto a constant voltage which is different from other constant voltages applied to the other accelerating electrodes such that the kinetic energy of the accelerated ions are continually increased toward the side of said mass spectrometer.

21. A mass spectrometry apparatus according to claim 20, wherein the voltage difference between the voltages applied to the adjacent two ion accelerating electrodes provided adjacent to said skimmer is smaller than the voltage difference between the voltages applied to the adjacent two ion accelerating electrodes provided adjacent to said mass spectrometer.

* * * * *